United States Patent [19]
Hardy et al.

[11] Patent Number: 6,088,488
[45] Date of Patent: Jul. 11, 2000

[54] VASCULAR IMAGING WITH ADAPTIVE AVERAGING

[75] Inventors: Christopher Judson Hardy, Schenectady; Rupert William Meldrum Curwen, Ballston Lake, both of N.Y.

[73] Assignee: General Electric Company, Schenectady, N.Y.

[21] Appl. No.: 09/062,417

[22] Filed: Apr. 17, 1998

[51] Int. Cl.[7] .............................. G06K 9/00; G06K 9/64; G06K 9/36
[52] U.S. Cl. ............................ 382/278; 382/130; 382/283
[58] Field of Search ..................................... 382/129–134, 382/205, 278, 280, 282, 283, 295, 273; 364/726.01, 728.03

[56] References Cited

U.S. PATENT DOCUMENTS

| | | | |
|---|---|---|---|
| 5,020,113 | 5/1991 | Lo et al. | 382/42 |
| 5,054,045 | 10/1991 | Whiting et al. | 378/99 |
| 5,293,574 | 3/1994 | Roehm et al. | 378/98.2 |
| 5,361,307 | 11/1994 | Hartley et al. | 382/1 |
| 5,431,161 | 7/1995 | Ryals et al. | 128/653.1 |
| 5,550,937 | 8/1996 | Bell et al. | 382/239 |
| 5,623,560 | 4/1997 | Nakajima et al. | 382/295 |
| 5,690,111 | 11/1997 | Tsujino | 128/660.04 |
| 5,724,496 | 3/1998 | Givens et al. | 345/440 |
| 5,787,889 | 8/1998 | Edwards et al. | 128/660.07 |

OTHER PUBLICATIONS

Weixin Xia and Weixue Lu, "Correspondence Analysis for Regional Tracking in Coronary Arteriograms", IEEE Transactions On Medical Imaging, vol. II, No. 2, 11(1992) Jun., NY, US, pp. 153–160.

Pratt, Digital Image Processing, Second Edition, Wiley & Sons, Inc., pp. 662–663, 1991.

*Primary Examiner*—Amelia Au
*Assistant Examiner*—Martin E. Miller
*Attorney, Agent, or Firm*—Jean K. Testa; Donald S. Ingraham

[57] ABSTRACT

A reference image R is selected and a region of interest (ROI) is interactively selected encompassing a desired structure from a sequence of images of a moving structure. This ROI is cross-correlated with other real-time images by multiplication in the Fourier frequency domain, to determine if the desired structure is present in the image. If the structure is present, this image may be averaged with other images in which the structure is present to produce higher resolution adaptively averaged images. This invention is particularly useful in imaging coronary vessels. In an alternative embodiment, the offset of the desired structure may be calculated in a series of images. The images may then be sorted by this offset, and played back in that order to provide a "movie-like" display of the desired structure moving with the periodic motion.

10 Claims, 3 Drawing Sheets

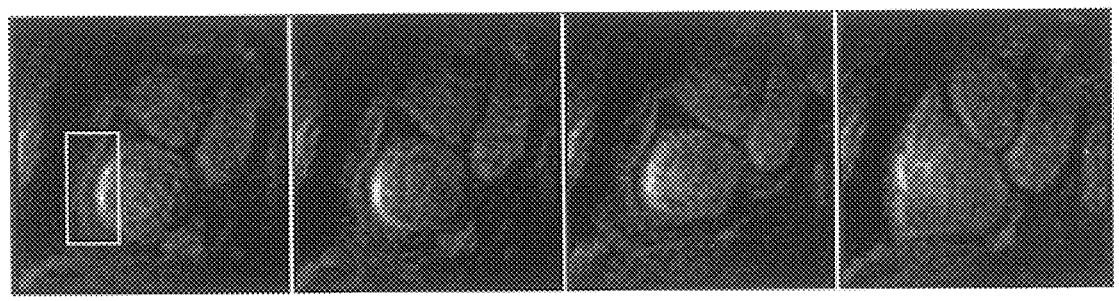
Fig. 1　　Fig. 2　　Fig. 3　　Fig. 4
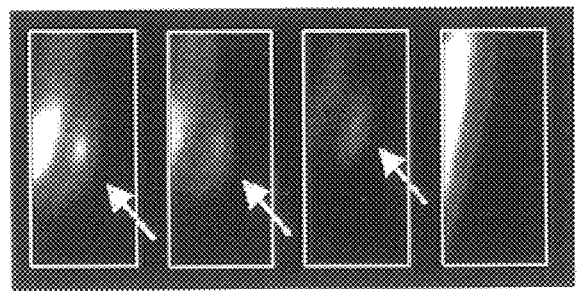 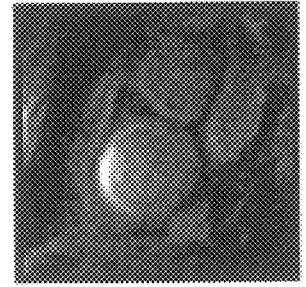
Fig. 5　Fig. 6　Fig. 7　Fig. 8　　　　Fig. 9

VASCULAR IMAGING WITH ADAPTIVE AVERAGING

CROSS REFERENCE TO PENDING APPLICATIONS

This is related to pending U.S. patent application 08/794,981 filed Feb. 8, 1997 "Fast Segmentation Of Cardiac Images" by Richard Hartley, Rupert Curwen, and Harvey Cline.

BACKGROUND OF THE INVENTION

1. Scope of the Invention

The present invention relates to image processing and more specifically to imaging structures having motion defined by a cycle.

2. Related Prior Art

Moving structures are difficult to image, especially if an imaging plane is set in space with the structure moving in and out of the imaging plane. This is especially difficult when a second periodic motion is added. For example, imaging of structures in a subject which is breathing causes a periodic motion of internal structures. This is further complicated by the beating motion of the heart if the structure is on, or near the heart. The beating of the heart is a complex compressional and twisting motion superimposed on the respiratory motion.

It is often desirable to acquire images of moving structures, such as in coronary angiography, where images are acquired of vessels in a beating heart. For image enhancement purposes, several images are averaged to reduce image noise, and improve visualization.

MR coronary angiography has typically been performed using either breath-held, oblique single-slice techniques, or respiratory-gated 3D techniques. Repeated breath holding may not be feasible for some coronary patients, and navigation techniques to date have not generally provided a robust method which works over a range of different breathing patterns in a variety of patients. Moreover, in both of these approaches, success or failure is often not apparent for some time after the start of imaging. The purpose of this study was to develop a robust, non-breath-held technique for coronary MRI based on adaptive averaging.

Currently, there is a need for an imaging method which creates clearer images of moving structures than previously possible.

SUMMARY OF THE INVENTION

High quality real-time images of a desired structure having periodic motion are acquired from a subject.

Several images are captured and displayed to a user. The user interactively selects an image containing the desired structure as a reference image R.

A region of interest (ROI1) is identified on reference image R encompassing the desired structure.

ROI1 is then cross-correlated with each successive captured image to result in a cross-correlation image. In the most efficient embodiment, cross-correlation is performed by multiplication in the Fourier, or k-space, domain.

A second region of interest is defined in the center of the cross-correlation image. When the cross-correlation image shows a peak within the region of interest, and more than a predetermined distance away from an edge of the region of interest, a "usable" image is identified.

A number of usable images are acquired and may be shifted and averaged, or sorted by their offsets and only those with similar offsets are averaged.

This produces averaged images with less blurring, since there is compensation for offsets. Also, averaging provides a higher quality image.

In an alternative embodiment, feedback is provided to the data source when the current image is a "useable" image. Additional information is acquired to augment the original raw data, and a higher-resolution image results.

OBJECTS OF THE INVENTION

An object of the present invention is to provide a system which provides high signal-to-noise images of structures having periodic motion.

Another object of the present invention is to provide high signal-to-noise images of structures of subjects without requiring the subjects to hold their breath during imaging.

Another object of the present invention is to provide high signal-to-noise images of coronary structures of subjects while the subjects are breathing normally.

BRIEF DESCRIPTION OF THE DRAWINGS

The features of the invention believed to be novel are set forth with particularity in the appended claims. The invention itself, however, both as to organization and method of operation, together with further objects and advantages thereof, may be best understood by reference to the following description taken in conjunction with the accompanying drawing in which:

FIGS. 1–4 are real-time, ungated, non-breath-hold images of a cross section of a subject's heart.

FIGS. 5–8 are cross correlations of a region of interest 1 (ROI1) with each of FIGS. 1–4, respectively.

FIG. 9 is a cross sectional image of the subject acquired from averaging images of FIGS. 1–3.

DETAILED DESCRIPTION OF THE INVENTION

Figure 10:
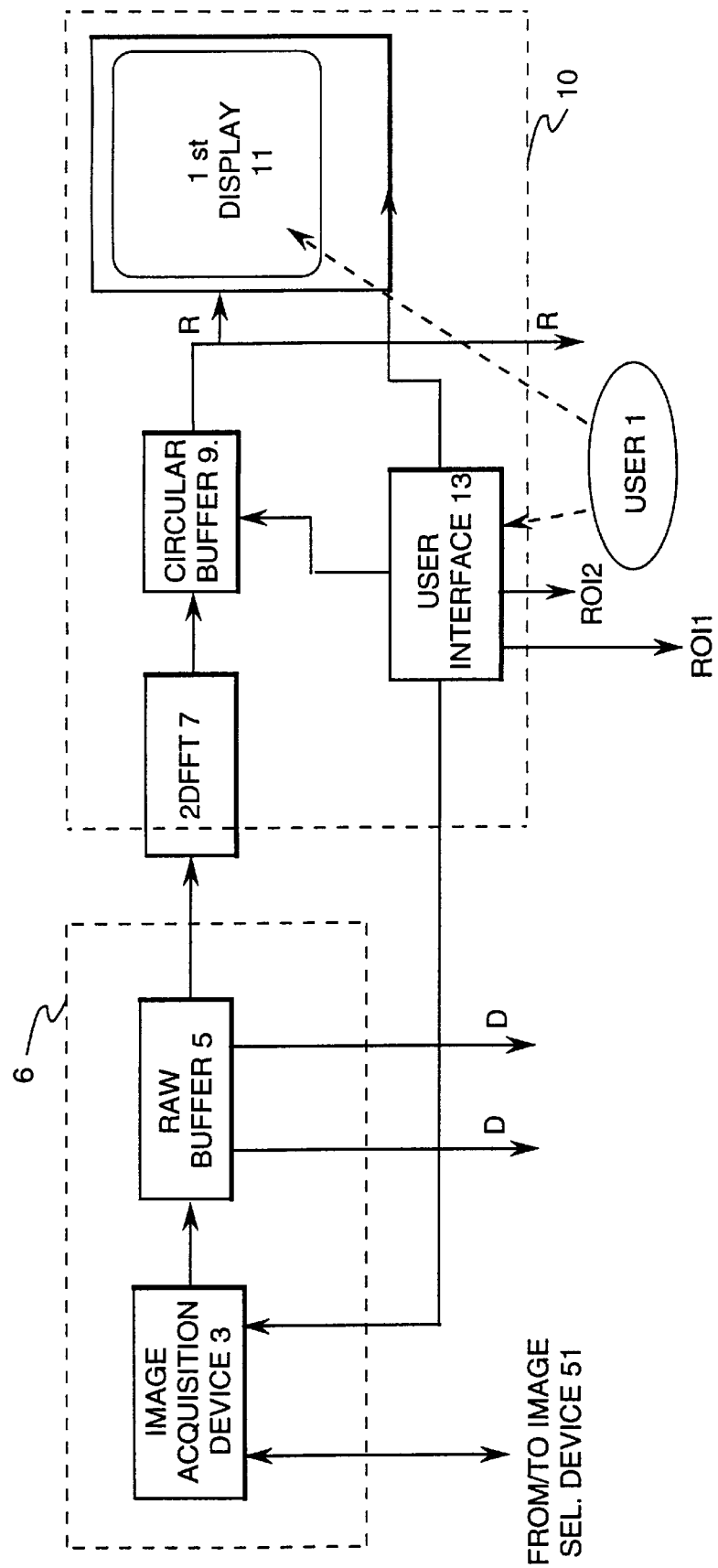
FIGS. 10 and 11 together are a simplified block diagram of an embodiment according to the present invention.

Several problems are encountered during imaging of moving structures. These apply for many different disciplines, but one of the best uses would be in coronary angiography. It will be explained for this use, but may be used for any imaging of structures undergoing periodic motion where the structure will pass in and out of an imaging plane.

Vessels of the heart may move in and out of an imaging plane due to beating of the subject's heart. The subject's breathing may also cause coronary vessels to move in and out of the imaging plane as the subject's chest moves.

If one were to identify images in which a desired coronary vessel was in an imaging plane, and use these images to create an average image, or a series of images, image quality would be greatly enhanced. Further, if one were to recover the offset of the coronary vessel in each image, one could use that offset to correct the position of the image before averaging with others in the sequence, thus avoiding blurring due to motion of the vessel in the imaging plane.

The user interacts with the system, while viewing a real-time imaging window, to define a region of interest (ROI1) around a desired vessel. This ROI1 is used to create a kernel which is cross-correlated with each new frame as it is acquired. To accelerate the cross-correlation, it is performed by multiplication in the Fourier (k-space) domain.

Frames which closely match the reference kernel produce a cross-correlation with a relatively large central peak.

Those frames in which the anatomy is translated within the plane will produce an offset in the peak, and those frames where the vessel has moved out of plane will have a relatively small signal in the central region. A peak threshold is used as a basis for rejecting frames. Images may be translated before averaging, if there is no rotation or deformation, and the offset of the peak from the center of the cross-correlation image indicates the translation required to align the original image. Images which have peaks which are greater than a predetermined spatial offset from the center, are also rejected.

In FIGS. 1 through 4, cardiac angiographic images which are not gated with either the breathing or cardiac cycles were acquired while the subject was breathing normally. Each image represents a specific time period during the cardiac cycle.

ROI1 was drawn around the vessel, in one of the images where the vessel was clearly visible. In FIG. 1 ROI1 is a white box which encompasses most of a coronary artery which is the light colored line. This same artery can be seen in FIGS. 2 and 3, however, in FIG. 4 the heart has moved into a position where that artery is no longer within the imaging plane.

The cross-correlations for FIGS. 1, 2, 3, 4 are shown in FIGS. 5, 6, 7, 8, respectively. FIG. 5, 6, 7 show prominent correlation peaks arising from the close correspondence between the base images (FIGS. 1, 2, 3) and the kernel (FIG. 5 is in fact an autocorrelation). The coronary in FIG. 3 is translated within the plane because of respiratory motion, and the correlation peak in FIG. 7 is likewise shifted up. A threshold was set as an acceptance criterion, and accepted frames from the full data set were averaged. The average of FIG. 1 and shifted FIGS. 2 and 3 resulted in FIG. 9, which is clearer than each image taken on its own.

Figure 11:
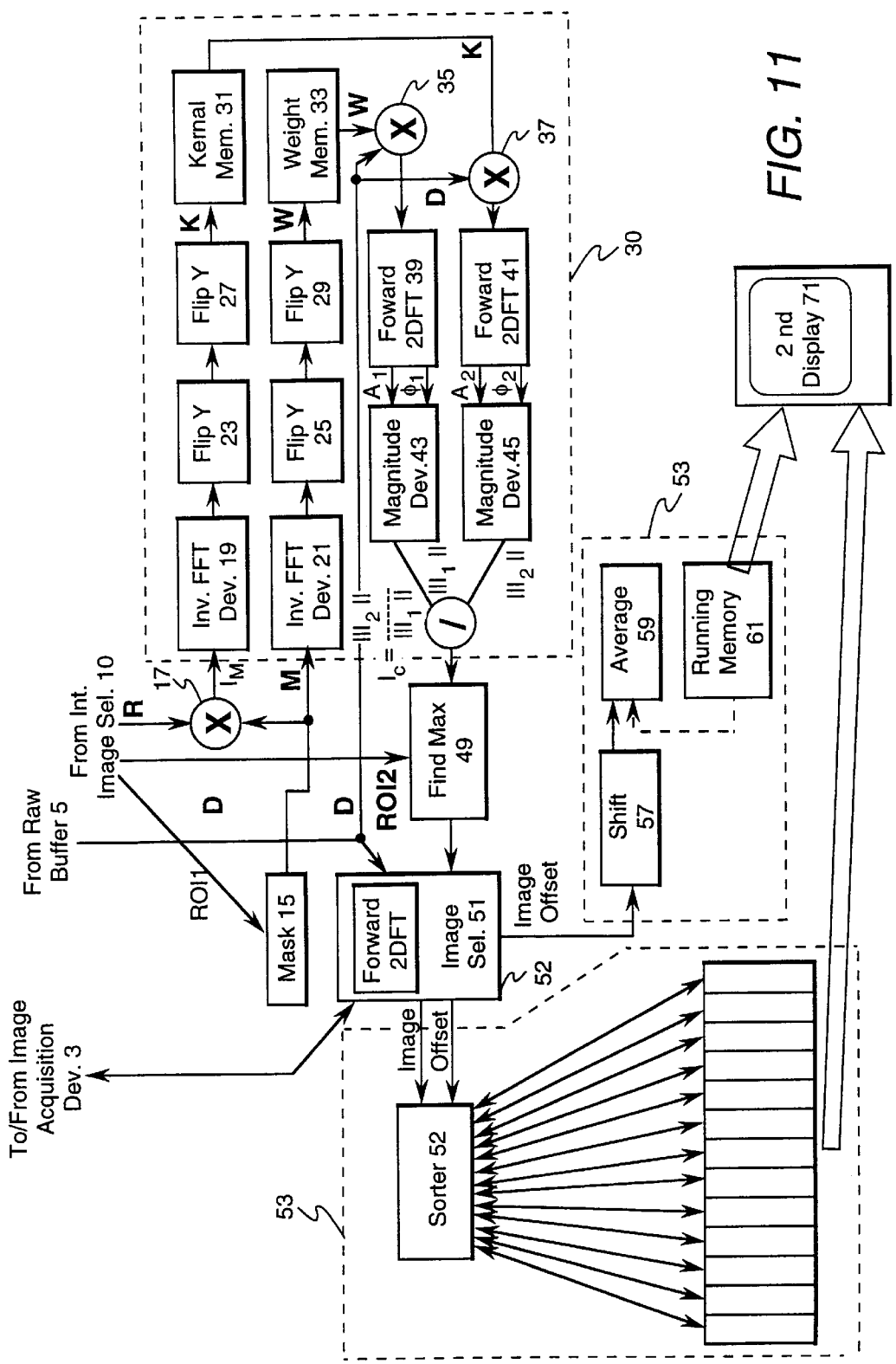

FIGS. 10 and 11 together show a simplified block diagram of the coronary angiography system of the present invention. A user 1 interacts with a user interface 13 which provides input to an image acquisition device 3 which may possibly be a magnetic resonance (MR) scanner, or other imaging device which acquires raw data in k-space. Image acquisition device 3 acquires image data, such as coronary angiography slices, and stores them in a raw buffer 5 which is unprocessed MR data and is still in the Fourier time domain, or "k-space". This raw data represents a plurality of MR images. The images acquisition device and the raw buffer act together as a data source 6.

The raw images are provided to a two-dimensional fast Fourier transform (2DFT) device 7 which transforms these back into the image space domain and fills a circular buffer 9 with images.

User 1 interacts with user interface 13 to select one of the images in circular buffer 9 interactively displayed on a display device 11, as a reference image R.

User 1 then interacts with user interface 13 to select a region of interest (ROI1) on reference image R which encompasses a desired structure to be imaged, such as a coronary vessel.

ROI1 from interface 13 is provided to a mask device 15 which creates a mask M of zeroes on all areas outside of the ROI1 and ones inside ROI1.

Mask M is provided to a multiplication device 17 along with selected reference image R from circular buffer 9 and multiplied to result in a masked image $I_m$ being essentially zeroes outside the ROI1 and a portion of reference image R inside of ROI1.

Mask M is provided to an inverse Fourier transform device 21 to provide a k-space representation of mask M.

This k-space representation of mask M has all of its coordinates flipped with respect to the x axis in a flip X device 25, and this result is passed to a flip Y device 29 which flips all of these coefficients with respect to the Y axis to result in a set of weighting coefficients W stored in weighting memory 33.

A similar process occurs to masked image $I_m$ with inverse FFT device 19, flip X device 23, flip Y device 27, respectively. The output of flip Y device 27 is a kernel set K which is stored in kernel memory 31.

Both kernel set K and weighting set W are in k-space. Kernel set K and weighting set W are used to multiply k-space image data D from raw buffer 5. A k-space image slice D from raw buffer 5 is provided to multipliers 35 and 37 with each weighting set W and kernel set K, respectively.

The result of multipliers 35 and 37 are provided to forward two dimensional Fourier transform (2DFT) devices 39 and 41, respectively, to produce image space representations $(A_1, \phi_1)$; $(A_2, \phi_2)$, respectively where A is the amplitude information, and $\phi$ is the phase information.

Magnitude devices 43 and 45 receive the phases and amplitudes from their respective forward 2DFT devices and create image magnitudes $\|I_1\|$ and $\|I_2\|$ representing the magnitude of the image at each point over the two dimensions of the image. At each location, $I_2$ is divided by $I_1$ to result in $I_c$ being the intensity of the correlation at that location. This results in a two-dimensional correlation map.

The elements encompassed by the dashed line perform a correlation in k-space, and are collectively referred to as a k-space correlation device 30.

A find max device 49 determines if a peak, being a local maximum intensity of $I_c$ over a second region of interest (ROI2) centered within the two dimensional cross correlation image field. ROI2 may be predetermined and stored, or may be user provided through user interface 13.

The location of the largest image intensity $I_c$ on the correlation map within ROI2 is subtracted from the center of the image to determine an offset. The height of the maximum correlation image intensity $I_c$ is the maximum correlation value R.

An image selection device 51 receives R in the offset from find max device 49, and also receives a k-space image from raw buffer 5.

Image selector 51 has logic predefined in it to determine if there is a peak in the correlation map, and also determines if the peak is within a predetermined distance from the edges of the correlation image. It may also determine if there is no peak but is steadily increasing correlation intensity values $I_c$ toward the edge of the ROI. This indicates that the ROI1 does not overlap the coronary vessels of the correlated image. If this is the case, the image is discarded and another image is provided to multipliers 35 and 37 with the process repeated up until this point.

However, if image selection device 51 determines that there is a peak $I_c$ and it is more than a minimum distance from the edge of ROI, it determines that this is a good image, a "usable" image, and a forward 2DFT device 52 transforms the it into image space and provides the image to a router device 53 along with the offset information.

In one embodiment router 53 merely stores images in a segmented memory 55 which has a plurality of locations each capable of holding the information representing an image slice.

In a second embodiment, router 53 receives more images and offsets than the number of bins in memory 55. A sorter 52 within router 53 then stores images with a predetermined offset range in each of the bins in segmented memory 55. Each additional image placed in a bin is averaged with an ongoing average of all the previous images stored in that bin.

This results in an "averaged movie", in which heart motion is essentially removed, and the coronary is seen moving up and down with respiration.

In still another embodiment, router 53 may be embodied by a shift device 57 connected to image selection device 51. It receives the images and their offsets and shifts each image by its offset to normalize the images, then provides the shifted image to an averager 59. Averager 59 also receives the contents already in a running memory 61, being a running image average. Averager then averages these images and stores them as a new running average in running memory 61. Each of these embodiments will have different uses and results.

This adaptively averaged image shows marked improvement in signal-to-noise ratio (SNR) relative to the real-time images. Adaptive averaging is feasible for coronary imaging.

In still another alternative embodiment, image acquisition device 3 may be coupled to, and responsive to, image selection device 51. Images may be acquired in a normal, or abbreviated manner to increase the speed of acquisition during normal imaging. However, when image selection device 51 determines that there is the desired structure in the current image D, indicated by a high correlation peak in correlation image, a signal is sent to image acquisition device 3 to acquire addition image information. This may mean that image acquisition device 3 samples lower spatial frequencies in k-space during quick acquisitions, but samples higher spatial frequencies upon receiving the signal from image selection device 51. The additional information may be passed directly to, image selection device 51, or pass through raw buffer first, and is intended to augment the already acquired raw image data D. This allows higher resolution images to be acquired when the desired structure is visible, while acquiring lower resolution, "quick" images at other times.

Since there is a first display 11 and a second display 71, at least two different representations may be simultaneously displayed to user 1. First display 11 may run real-time image of the subject's beating heart, or may disconnect and play any, or all, of the images saved in circular buffer 9.

Second display may play the "averaged movie" while comparing this to the real-time display of 1$^{st}$ display means 11, or have an averaged image of running memory 61 which is updated according to users input. It is possibly to have the updating proceed continuously.

Second display 71 may also play all, or any, of the images in memory 55 which may be continuously updated or static.

RESULTS

The coronary image of FIGS. 1–4 were acquired using a spiral fluoroscopy pulse sequence on a high-performance gradient system (Signa Horizon EchoSpeed, GE Medical Systems). The scanner was controlled from an UltraSparc 2 and images transferred back, reconstructed, and displayed to produce a real-time view of the beating heart. The 6-interleave spiral pulse sequence produced a matrix size of 128×128, with 5 complete new images per second and 9 reconstructions per second. Screen-based tools were used to interactively locate optimal coronary scan planes within 10–20 seconds, prior to adaptive coronary imaging.

Real-time spiral fluoroscopy with adaptive averaging shows potential as a robust technique for coronary MRI. It requires no breath-holding, no separate navigation sequence, and no ECG gating. Moreover, it allows continuous visualization of the vessel of interest from the start of imaging. Interactive location of coronary scan planes can be readily interleaved with adaptive averaging during real-time imaging of those scan planes.

While several presently preferred embodiments of the novel invention has been described in detail herein, many modifications and variations will now become apparent to those skilled in the art. It is, therefore, to be understood that the appended claims are intended to cover all such modifications and variations as fall within the true spirit of the invention.

What is claimed is:

1. A method for acquiring high-quality images of a desired structure having periodic motion in a series of images comprising the steps of:
   a) displaying the series of images to accept user-supplied input identifying a selected image containing the desired structure as a reference image R;
   b) identifying a region of interest ROI1 in reference image R encompassing the desired structure;
   c) cross-correlating ROI1 with each of the other images from the series of images to result in a series of cross-correlation images;
   d) defining a second region of interest ROI2 centered in each cross-correlation image;
   e) identifying images as "usable" images, which have a peak within ROI2 of their cross-correlation image more than a predetermined distance away from an edge of ROI2;
   f) processing only the "usable" images, to result in a higher quality processed image.

2. The method for acquiring high quality images of claim 1 wherein the step of performing a cross-correlation comprises the steps of:
   a) inverse Fourier transforming the reference image R within the ROI1 into a k-space image;
   b) flipping the k-space image with respect to its X coordinates;
   c) flipping the k-space image with respect to its Y coordinates to result in a kernel set K;
   d) creating a mask M having zeros outside of the ROI1 and ones inside of ROI1;
   e) inverse Fourier transforming mask M into a k-space image; flipping the k-space image of mask M with respect to its X coordinates;
   f) flipping the k-space image of mask M with respect to its Y coordinates to result in a weighting set W;
   g) multiplying the kernel set K and weighting set W each by a raw data image D to result in product K, and product W respectively;
   h) performing a 2D forward Fourier transform on product K and product W to result in amplitude and phase information ($A_2$, $\phi_2$), and ($A_1$, $\phi_1$); respectively;
   i) determining the magnitudes, $\|I_2\|$, $\|I_1\|$ from information ($A_2$, $\phi_2$), and ($A_1$, $\phi_1$); respectively; and
   j) determining a cross-correlation image $I_c$ according to:

$$I_c = \frac{\|I_2\|}{\|I_1\|}.$$

3. The method for acquiring high quality images of claim 1 wherein the cross-correlation is performed by multiplication in k-space to result in rapid cross-correlation.

4. The method for acquiring high quality images of a desired structure of claim 1 further comprising the steps of:
 a) calculating offsets from the location of cross-correlation peaks of usable images from a center point of their cross-correlation images;
 b) translating the usable images by the offset amount to correct for the offset; and
 c) averaging the translated images to result in processed images with reduced blurring.

5. The method for acquiring high quality images of a desired structure of claim 1 further comprising the steps of:
 a) calculating offsets from the location of cross-correlation peaks of usable images from a center point of their cross-correlation images;
 b) sorting images according to their offsets;
 c) playing back the images in their sorted order to provide an "averaged movie" which changes according to the offset.

6. The method for acquiring high quality images of a desired structure of claim 3 wherein:
 a) the images are coronary angiography images of a subject breathing during acquisition;
 b) the structure imaged is coronary vessel;
 c) offsets are due to breathing motion; and
 d) the "averaged movie" essentially removes heart motion.

7. A system for displaying high quality processed images derived from a series of images acquired from a desired structure having periodic motion comprising:
 a) a data source for acquiring a plurality of raw images in Fourier k-space, and for providing these images to connected elements;
 b) an interactive image selection device coupled to data source 6 for selecting and displaying user defined images, and operating to define an ROI1 on a user-selected reference image R;
 c) a mask device coupled to the interactive image selection device for operating to receive ROI1 and create a mask M having all zeroes outside of ROI1 and all ones inside of ROI1;
 d) a k-space correlation device coupled to interactive image selection device, mask device, and data sources, for creating a cross-correlation image $I_c$ from reference image R, mask M and raw data image D;
 e) a find max device coupled to the k-space cross-correlation device operating to calculate if a peak exists, and a peak height, and an offset of the peak from the center of the cross-correlation image $I_c$ for existing peaks;
 f) an image selection device coupled to find max device and from raw buffer, operating to receive the offset, and peak height, raw data image D, and determine if the peak height is greater than a predetermined threshold, and the offset is less than a predetermined threshold defining a "usable" image, and operating to performing a 2D Fourier transform on "usable" images;
 g) an image memory capable of storing and retrieving a plurality of images;
 h) a router coupled to image selection device, operating to receive the 2DFT representations of usable images and further process these images, then store these processed images in image memory; and
 i) a display device coupled to the image memory for displaying the processed images stored in image memory.

8. The system for displaying high quality processed images of claim 7 wherein the router comprises a sorter which processes images by sorting usable images provided to it according to their offset.

9. The system for displaying high quality processed images of claim 7 wherein the router comprises:
 a) a shift device for receiving image and offset translating each image at its offset;
 b) a running memory capable of storing image data, containing a running image average; and
 c) an averager coupled to the running memory and shift device, for receiving and averaging the running average image and the translated image from the shift device and storing the result in the running memory.

10. The system for displaying high quality processed images of claim 7, wherein:
 a) image acquisition device has operates in at least two modes, the first being "quick" acquisition of abbreviated images; and upon receiving a signal operates in a second mode being a high-resolution acquisition mode;
 b) the image selection device is connected to the image acquisition device, and sends a signal to image acquisition device when a current "usable" image is detected, causing it to acquire additional information which supplements the original raw data D.

* * * * *